United States Patent
Cosmescu

(10) Patent No.: US 10,702,334 B2
(45) Date of Patent: Jul. 7, 2020

(54) ULTRAPOLAR TELESCOPIC ELECTROSURGERY PENCIL

(71) Applicant: I.C. Medical, Inc., Phoenix, AZ (US)

(72) Inventor: Ioan Cosmescu, Phoenix, AZ (US)

(73) Assignee: I.C. Medical, Inc., Phoenix, AZ (US)

( * ) Notice: Subject to any disclaimer, the term of this patent is extended or adjusted under 35 U.S.C. 154(b) by 529 days.

(21) Appl. No.: 15/211,431

(22) Filed: Jul. 15, 2016

(65) Prior Publication Data

US 2018/0014875 A1    Jan. 18, 2018

(51) Int. Cl.
| | |
|---|---|
| *A61B 18/12* | (2006.01) |
| *A61B 18/14* | (2006.01) |
| *A61B 18/00* | (2006.01) |
| *A61B 17/00* | (2006.01) |

(52) U.S. Cl.
CPC .......... *A61B 18/149* (2013.01); *A61B 18/148* (2013.01); *A61B 2017/00991* (2013.01); *A61B 2018/00607* (2013.01); *A61B 2018/00958* (2013.01); *A61B 2018/1467* (2013.01)

(58) Field of Classification Search
CPC ...... A61B 18/1402; A61B 2018/00589; A61B 2018/00601; A61B 2018/00607; A61B 2018/1475

See application file for complete search history.

(56) References Cited

U.S. PATENT DOCUMENTS

| | | | |
|---|---|---|---|
| 4,202,337 A | | 5/1980 | Hren et al. |
| 4,545,375 A | * | 10/1985 | Cline ................ A61B 18/1402 200/302.2 |
| 4,802,476 A | | 2/1989 | Noerenberg |
| 4,823,791 A | * | 4/1989 | D'Amelio ............ A61B 18/14 219/234 |
| 4,850,353 A | | 7/1989 | Stasz et al. |
| 5,013,312 A | | 5/1991 | Parins et al. |
| 5,171,311 A | | 12/1992 | Rydell et al. |
| 5,626,577 A | * | 5/1997 | Harris ............... A61B 18/1402 606/41 |
| 5,733,283 A | * | 3/1998 | Malis .................... A61B 18/14 606/48 |
| 6,277,114 B1 | | 8/2001 | Bullivant et al. |
| 2005/0113825 A1 | | 5/2005 | Cosmescu |
| 2005/0273097 A1 | | 12/2005 | Ryan |
| 2006/0025757 A1 | | 2/2006 | Heim |
| 2009/0062791 A1 | * | 3/2009 | Lee .................... A61B 18/1402 606/45 |
| 2010/0049162 A1 | * | 2/2010 | Hameed ............ A61B 1/00082 604/500 |
| 2011/0202057 A1 | | 8/2011 | Thorne et al. |
| 2011/0224669 A1 | | 9/2011 | Podany |
| 2014/0236143 A1 | | 8/2014 | Ward |

OTHER PUBLICATIONS

International Search Report and the Written Opinion of the International Searching Authority from related PCT Application No. PCT/US2017/031137 dated Jul. 25, 2017.

* cited by examiner

*Primary Examiner* — Daniel W Fowler
(74) *Attorney, Agent, or Firm* — Zeman-Mullin & Ford, LLP

(57) ABSTRACT

An ultrapolar telescopic electrosurgery pencil/handpiece with or without smoke evacuation that is capable of cutting with a sharp non-conductive cutting end of an electrosurgery blade and cutting and coagulating with activation of active and return contacts both contained on each side of the electrosurgery blade.

25 Claims, 2 Drawing Sheets

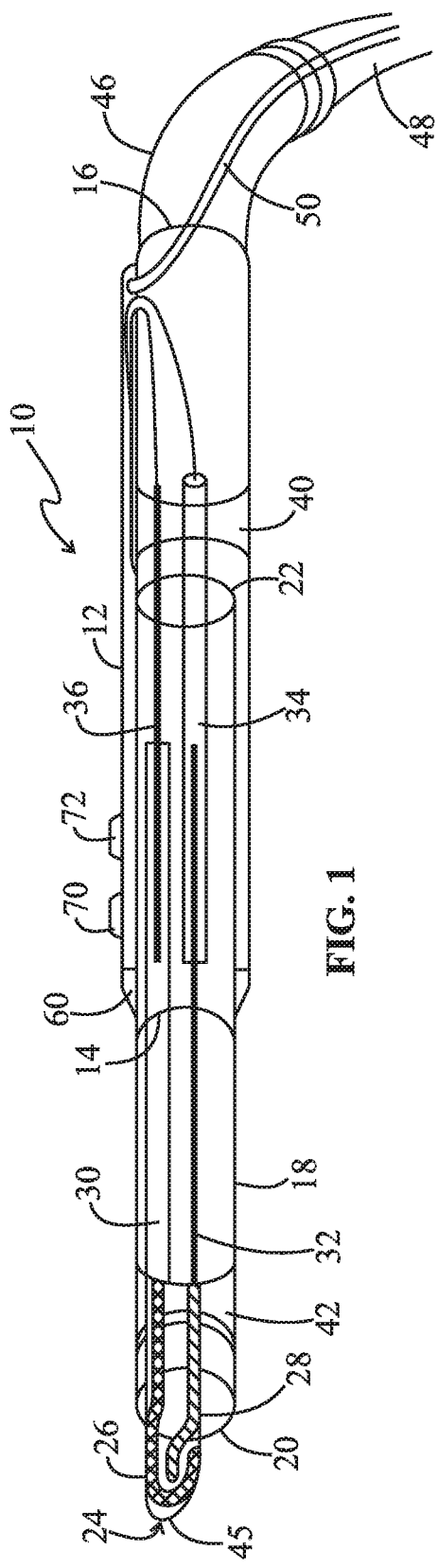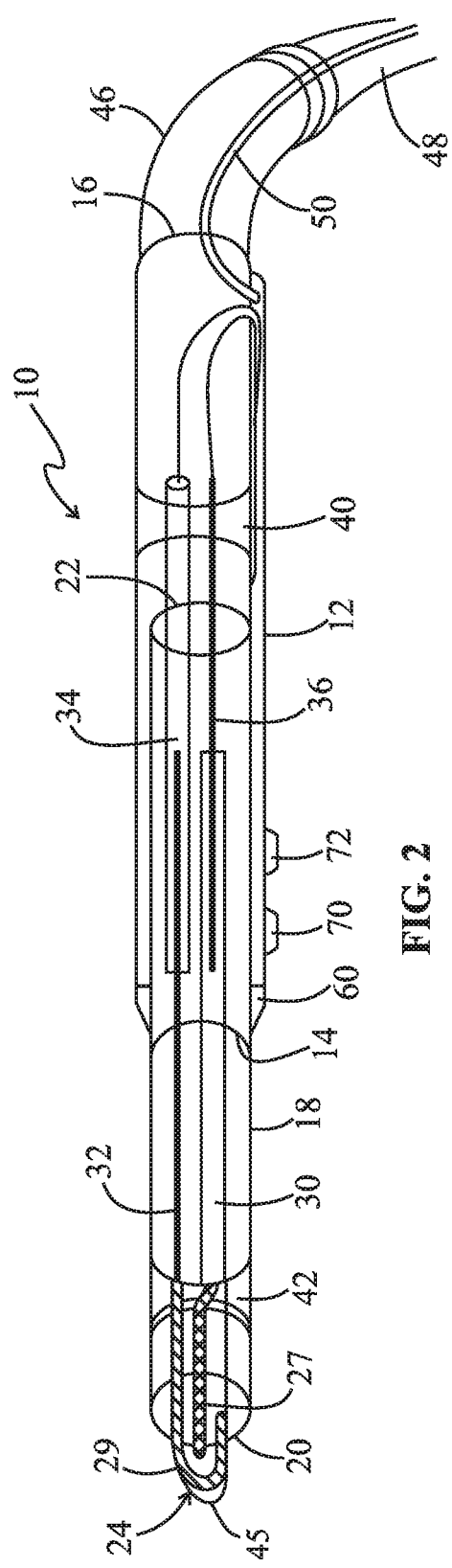

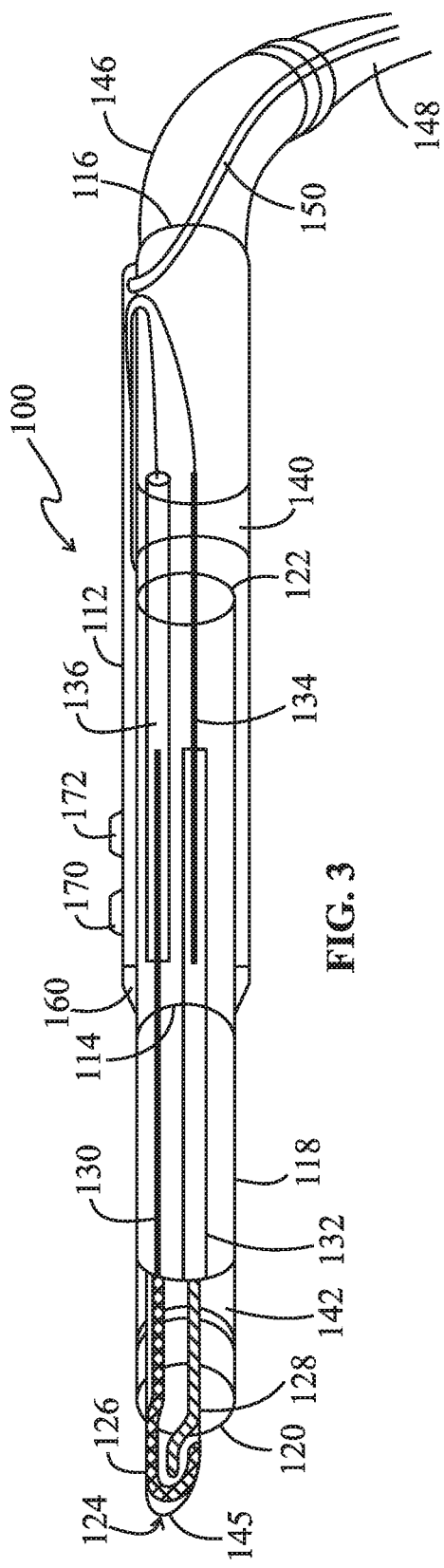
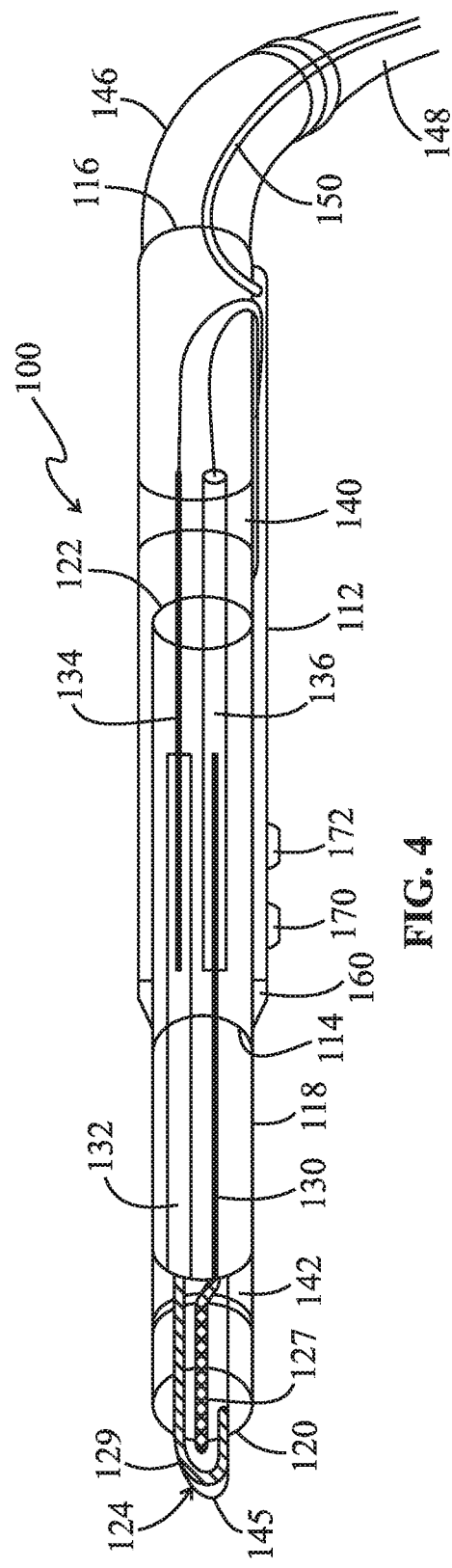

ULTRAPOLAR TELESCOPIC ELECTROSURGERY PENCIL

CROSS-REFERENCE TO RELATED APPLICATIONS

This application relates to patent application having Ser. No. 15/211,270 entitled "Ultrapolar Electrosurgery Blade And Ultrapolar Electrosurgery Pencil," filed Jul. 15, 2016, which is herein incorporated by reference in its entirety.

FIELD OF INVENTION

The present invention is generally directed to an ultrapolar telescopic electrosurgery pencil/handpiece that is capable of cutting with a sharp non-conductive cutting end of an electrosurgery blade and cutting or coagulating with activation of active and return electrodes both contained on the electrosurgery blade. The ultrapolar telescopic electrosurgery pencil/handpiece of the present invention may also be capable of evacuating smoke and/or debris form the surgical site. The ultrapolar telescopic electrosurgery pencil/handpiece of the present invention includes a handpiece member with a first end and second end, a hollow telescopic member with a first end and a second end where the hollow telescopic member is concentrically positioned within the first end of the handpiece, an electrosurgery blade with both active and return contacts positioned within the first end of the hollow telescopic member, a first hollow conductive tubular member in contact with either the active or return contact of the electrosurgery blade contained within the hollow telescopic member, a first solid cylindrical member in contact with whichever contact of the electrosurgery blade that is not in contact with the first hollow conductive tubular member and contained within the hollow telescopic member, a second hollow conductive tubular member contained within the handpiece member such that at least a portion of the first solid cylindrical member is contained within at least a portion of the second hollow conductive tubular member, and a second solid cylindrical member contained within the handpiece member such that at least a portion of the second solid cylindrical member is contained within at least a portion of the first hollow conductive tubular member.

BACKGROUND OF THE INVENTION

Electrosurgery uses an RF electrosurgical generator (also known as an electrosurgical unit or ESU) and a handpiece with an electrode to provide high frequency, alternating radio frequency (RF) current input at various voltages to cut or coagulate biological tissue. The handpiece may be a monopolar instrument with one electrode or a bipolar instrument with two electrodes. When using a monpolar instrument, a return electrode pad is attached to the patient and the high frequency electrical current flows from the generator, to the monopolar instrument, through the patient to the patient return electrode pad, and back to the generator. Monopolar electrosurgery is commonly used due to its versatility and effectiveness. However, the excessive heat generated with monopolar electrosurgery can cause excessive tissue damage and necrosis of the tissue because the return electrode positioned on the back of the patient causes high voltage and high RF energy to pass through the patient.

In bipolar electrosurgery, active output and patient return functions both occur at the surgery site because both the active and return electrodes are contained in the bipolar instrument. Therefore, the path of the electrical current is confined to the biological tissue located between the active and return electrodes. Although bipolar electrosurgery enables the use of lower voltages and less energy and thereby reduces or eliminates the likelihood of tissue damage and sparking associated with monopolar electrosurgery, it has limited ability to cut and coagulate large bleeding areas.

Accordingly, there is a need for an electrosurgery instrument such as an electrosurgery handpiece/pencil that allows for both cutting and coagulation of large areas of tissue without the tissue damage and which eliminates passing of energy through the patient. A telescopic ultrapolar electrosurgery handpiece/pencil having an electrosurgery blade with a sharp cutting edge and both active and return electrodes positioned on opposing sides of the electrosurgery blade would enable both precise cutting and coagulation of large areas of biological tissue. Further, such an ultrapolar telescopic electrosurgery handpiece/pencil would enable a user or surgeon to more easily and efficiently access the surgical site with enhanced viewing capability by extending the telescopic member of the handpiece/pencil as well as the ultrapolar electrosurgery blade positioned within the telescopic member of the handpiece/pencil. The ultrapolar telescopic electrosurgery handpiece/pencil of the present invention also enables a user or surgeon to evacuate smoke and/or debris from the surgical site while being able to perform precise cutting at the surgical site as well as cutting and coagulation of large biological tissue areas located at the surgical site.

SUMMARY OF THE INVENTION

The present invention is directed to an ultrapolar telescopic electrosurgery handpiece/pencil that is capable of performing precise cutting at a surgical site as well as cutting and coagulation of large biological tissue areas at the surgical site. The ultrapolar telescopic electrosurgery pencil of the present invention is also capable of effectively and efficiently accessing a surgical site while providing enhanced visibility at the surgical site by extending the telescopic member of the ultrapolar telescopic electrosurgery handpiece/pencil and the ultrapolar electrosurgery blade contained within the telescopic member while at the same time evacuating smoke and/or debris form the surgical site.

In one exemplary embodiment, the ultrapolar telescopic electrosurgery handpiece/pencil of the present invention includes a handpiece member having first and second ends, a hollow telescopic member having first and second ends with at least a portion of the hollow telescopic member concentrically positioned within the first end of the handpiece member, an electrosurgery blade having both active and return contacts positioned within the first end of the hollow telescopic member, a first hollow conductive tubular member in contact with the active contact of the electrosurgery blade and contained within the hollow telescopic tubular member, a first solid conductive cylindrical member in contact with the return contact of the electrosurgery blade and contained within the hollow telescopic member, a second hollow conductive tubular member contained within the handpiece member such that at least a portion of the first solid cylindrical member is contained within at least a portion of the second hollow conductive tubular member, and a second solid cylindrical member contained within the handpiece member such that at least a portion of the second solid cylindrical member is contained within at least a portion of the first hollow conductive tubular member. The handpiece member may further include a smoke evacuation channel in communication with an interior of the hollow telescopic tubular member for evacuating smoke and/or debris form the surgical site.

The ultrapolar telescopic electrosurgery handpiece/pencil may further include a first support member positioned within the handpiece member with at least a portion of the second solid conductive cylindrical member and at least a portion of the second hollow conductive tubular member passing through the first support member and/or a second support member positioned within the hollow telescopic member with at least a portion of the active contact of the electrosurgery blade and at least a portion of the return contact of the electrosurgery blade passing through the second support member. The ultrapolar telescopic electrosurgery handpiece/pencil may also include a swivel member connected to the second end of the handpiece member to enable a vacuum tube connected to the swivel member to twist about or around an electrical cord connected to the handpiece member thereby facilitating a surgeon's use of the ultrapolar telescopic electrosurgery handpiece/pencil by reducing the drag or pulling down of the end of the ultrapolar telescopic electrosurgery handpiece/pencil opposite the electrosurgery blade.

The first and second hollow conductive tubular members and the first and second solid conductive cylindrical members of the ultrapolar telescopic electrosurgery handpiece/pencil of the present invention may be made of stainless steel, copper, and/or titanium. Further, the first and second hollow conductive tubular members may each have an insulator on their outer surfaces.

The electrosurgery blade of the ultrapolar telescopic electrosurgery handpiece/pencil may include a non-conductive planar member having opposing planar sides with both an active contact and a return contact on each opposing planar side of the non-conductive planar member. The electrosurgery blade may further include a non-conductive sharp cutting tip that may be formed from the non-conductive planar member and the non-conductive sharp cutting tip and the non-conductive planar member may comprise a ceramic material.

The ultrapolar telescopic electrosurgery handpiece/pencil of the present invention may also include a locking member to lock the hollow telescopic tubular member in place relative to the handpiece member. The ultrapolar telescopic electrosurgery handpiece/pencil of the present invention may also include at least one activation button for cutting and at least one activation button for coagulation.

In another exemplary embodiment, the ultrapolar telescopic electrosurgery handpiece/pencil of the present invention includes a handpiece member having first and second ends, a hollow telescopic member having first and second ends with at least a portion of the hollow telescopic member concentrically positioned within the first end of the handpiece member, an electrosurgery blade having both active and return contacts positioned within the first end of the hollow telescopic member, a first solid conductive cylindrical member in contact with the active contact of the electrosurgery blade and contained within the hollow telescopic tubular member, a first hollow conductive tubular member in contact with the return contact of the electrosurgery blade and contained within the hollow telescopic tubular member, a second solid conductive cylindrical member contained within the handpiece member such that at least a portion of the second solid cylindrical member is contained within at least a portion of the first hollow conductive tubular member, and a second hollow conductive tubular member contained within the handpiece member such that at least a portion of the first solid cylindrical member is contained within at least a portion of the second hollow conductive tubular member. Like the previously described exemplary embodiment, the handpiece member may further include a smoke evacuation channel in communication with an interior of the hollow telescopic tubular member for evacuating smoke and/or debris form the surgical site.

This second exemplary embodiment of the ultrapolar telescopic electrosurgery handpiece/pencil may include a first support member positioned within the handpiece member with at least a portion of the second solid cylindrical member and at least a portion of the second hollow conductive tubular member passing through the first support member and/or a second support member positioned within the hollow telescopic member with at least a portion of the active contact of the electrosurgery blade and at least a portion of the return contact of the electrosurgery blade passing through the second support member. This embodiment may also include a swivel member connected to the second end of the handpiece member to enable a vacuum tube connected to the swivel member to twist about or around an electrical cord connected to the handpiece member thereby facilitating a surgeon's use of the ultrapolar telescopic electrosurgery handpiece/pencil by reducing the drag or pulling down of the end of the ultrapolar telescopic electrosurgery handpiece/pencil opposite the electrosurgery blade.

Like the first exemplary embodiment, the first and second hollow conductive tubular members and the first and second solid conductive cylindrical members of the second exemplary embodiment of the ultrapolar telescopic electrosurgery handpiece/pencil of the present invention may be made of stainless steel, copper, and/or titanium. Further, the first and second hollow conductive tubular members may each have an insulator on their outer surfaces. In addition, the electrosurgery blade of the second exemplary embodiment of the ultrapolar telescopic electrosurgery handpiece/pencil may include a non-conductive planar member having opposing planar sides with both an active contact and a return contact on each opposing planar side of the non-conductive planar member. The electrosurgery blade may further include a non-conductive sharp cutting tip that may be formed from the non-conductive planar member and the non-conductive sharp cutting tip and the non-conductive planar member may comprise a ceramic material.

Further, like the first exemplary embodiment, the second exemplary embodiment of the ultrapolar telescopic electrosurgery handpiece/pencil of the present invention may also include a locking member to lock the hollow telescopic tubular member in place relative to the handpiece member and at least one activation button for cutting and at least one activation button for coagulation.

BRIEF DESCRIPTION OF THE DRAWINGS

The subject invention will hereinafter be described in conjunction with the appended drawing figures, wherein like numerals denote like elements, and FIG. 1 is a side perspective view of a first exemplary embodiment of the ultrapolar telescopic electrosurgery handpiece/pencil of the present invention showing the interior components of the ultrapolar telescopic electrosurgery handpiece/pencil as they would appear if one could see inside of the handpiece/pencil;

FIG. 2 is the same as the view shown in FIG. 1 but with the ultrapolar telescopic electrosurgery handpiece/pencil shown rotated 180 degrees relative to the swivel member of the ultrapolar telescopic electrosurgery handpiece/pencil which is maintained in the same position when the handpiece member and the hollow telescopic member of the ultrapolar telescopic electrosurgery handpiece/pencil are rotated 180 degrees;

FIG. 3 is a side perspective view of a second exemplary embodiment of the ultrapolar telescopic electrosurgery handpiece/pencil of the present invention showing the interior components of the ultrapolar telescopic electrosurgery handpiece/pencil as they would appear if one could see inside of the handpiece/pencil; and FIG. 4 is the same as the view shown in FIG. 3 but with the ultrapolar telescopic electrosurgery handpiece/pencil shown rotated 180 degrees relative to the swivel member of the ultrapolar telescopic electrosurgery handpiece/pencil which is maintained in the same position when the handpiece member and the hollow telescopic member of the ultrapolar telescopic electrosurgery handpiece/pencil are rotated 180 degrees.

DETAILED DESCRIPTION OF EXEMPLARY EMBODIMENTS

The exemplary embodiments of the ultrapolar telescopic electrosurgery handpiece/pencil of the present invention enable a user or surgeon to perform precise cutting as well as coagulation. The ultrapolar telescopic electrosurgery handpiece/pencil of the present invention also enables simultaneous evacuation of smoke and/or debris from the surgical site as well as the ability to telescopically adjust the length of the ultrapolar telescopic electrosurgery handpiece/pencil depending on the type of access needed to the surgical site. The ultrapolar telescopic electrosurgery handpiece/pencil of the present invention also includes a swivel member connected to the end of the handpiece member opposite the electrode to enable a vacuum tube connected to the swivel member to twist about or around an electrical cord connected to the handpiece member thereby facilitating a surgeon's use of the ultrapolar telescopic electrosurgery handpiece/pencil by reducing the drag or pulling down of the end of the ultrapolar telescopic electrosurgery handpiece/pencil during electrosurgery. Ultrapolar telescopic electrosurgery handpiece/pencil is used interchangeably with electrosurgery handpiece/pencil, electrosurgery handpiece, electrosurgery pencil, and handpiece/pencil throughout the specification and all are meant to refer to the same subject of the invention.

FIG. 1 is a side perspective view of a first exemplary embodiment of the ultrapolar telescopic electrosurgery handpiece/pencil 10 of the present invention showing the interior components of the ultrapolar telescopic electrosurgery handpiece/pencil 10 as they would appear if one could see inside of the handpiece/pencil 10. Ultrapolar telescopic electrosurgery handpiece/pencil 10 includes a handpiece member 12 having a first end 14 and a second end 16, a hollow telescopic member 18 having a first end 20 and a second 22 where at least a portion of the hollow telescopic member 18 is concentrically positioned within the first end 14 of handpiece member 12, an electrosurgery blade 24 having both an active contact 26 and a return contact 28 positioned within the first end 20 of hollow telescopic member 18, a first hollow conductive tubular member 30 in contact with active contact 26 of electrosurgery blade 24 and contained within the hollow telescopic member 18, a first solid conductive cylindrical member 32 in contact with return contact 28 of electrosurgery blade 24 and contained within the hollow telescopic member 18, a second hollow conductive tubular 34 contained within the handpiece member 12 such that at least a portion of the first solid cylindrical member 32 is contained within at least a portion of the second hollow conductive tubular member 34, and a second solid conductive cylindrical member 36 contained within the handpiece member 12 such that at least a portion of the second solid conductive cylindrical member 36 is contained within at least a portion of the first hollow conductive tubular member 30. It will be understood by those skilled in the art that other means for connecting active contact 26 and return contact 28 of electrosurgery blade 24 to a circuit board located in or on handpiece member 12 for activating cutting and/or coagulation may be utilized, such as wires each coated with an insulator, for example, as long as the insulated wires are durable and capable of ensuring that the respective wires connected to the active and return contacts do not come into contact with one another. However, the solid conductive cylindrical members and the hollow conductive tubular members that are described with reference to the exemplary embodiments shown and described herein are considered to be a superior means for connecting the active and return contacts of the ultrapolar electrosurgery blade to the circuit board that enables activation of cutting and/or coagulation with the handpiece/pencil. In addition, the utilization of the solid conductive cylindrical members and the hollow conductive tubular members that are described with reference to the exemplary embodiments shown and described herein create a handpiece/pencil that is much less likely to be subject to failure and a handpiece/pencil that is much less likely to malfunction and result in an injury to a patient and or a user/surgeon during use of the handpiece/pencil.

As can be seen in the exemplary embodiment shown in FIG. 1, the electrosurgery pencil/handpiece of the present invention has a handpiece member 12 and a hollow telescopic member 18 which both have channels therein that are in continuity with one another to enable evacuation of smoke and/or debris from the surgical site. During evacuation, the smoke and/or debris passes through the continuous channel and around the first and second hollow conductive tubular members 30, 34 and the first and second solid conductive cylindrical members 32, 36 that are contained in the continuous channel. In addition, a first support member 40 is positioned within the handpiece member 12 such that at least a portion of the second solid conductive cylindrical member 36 and at least a portion of the second hollow conductive tubular member 34 pass through the first support member 40. Further, a second support member 42 is positioned within the hollow telescopic member 18 such that at least a portion of the active contact 26 of electrosurgery blade 24 and at least a portion of return contact 28 of electrosurgery blade 24 pass through the second support member 42. The first and second hollow conductive tubular members 30, 34 and the first and second solid conductive cylindrical members 32, 36 may be made of stainless steel, copper, and/or titanium and the outer surfaces of the first and second hollow conductive tubular members 30, 34 may each be covered with an insulator.

The electrosurgery blade 24 is an ultrapolar electrosurgery blade having a non-conductive planar member with opposing planar sides and both an active contact 26 and a return contact 28 on each opposing planar side of the non-conductive planar member. The ultrapolar electrosurgery blade 24 further includes a non-conductive sharp cutting tip 45. The non-conductive sharp cutting tip 45 may be formed from the non-conductive planar member and both may made of a ceramic material.

Ultrapolar telescopic electrosurgery handpiece/pencil 10 also includes a swivel member 46 connected to the second end 16 of the handpiece member 12 such that the swivel member 46 rotates relative to the handpiece member 12. The swivel member 46 enables a vacuum tube 48 connected to the swivel member to twist about or around an electrical cord 50 connected to the handpiece member 12 thereby facilitating a surgeon's use of the ultrapolar telescopic electrosurgery handpiece/pencil 10 by reducing the drag or pulling down of the end of the ultrapolar telescopic electrosurgery handpiece/pencil 10 during electrosurgery.

FIG. 2 is the same as the view shown in FIG. 1 but with the ultrapolar telescopic electrosurgery handpiece/pencil 10 shown rotated 180 degrees relative to the swivel member 46 of the ultrapolar telescopic electrosurgery handpiece/pencil 10 which is maintained in the same position when the handpiece member 12 and the hollow telescopic member 18 of the ultrapolar telescopic electrosurgery handpiece/pencil 10 are rotated 180 degrees. As can be seen in FIG. 2, ultrapolar electrosurgery blade 24 also has a second active contact 27 and a second return contact 29 located on the opposing planar side of the non-conductive planar member that is opposite the opposing planar side that contains active contact 26 and return contact 28. As can be seen in FIGS. 1 and 2, active contact 26 and second active contact 27 are both in contact with, or in communication with, first hollow conductive tubular member 30 and return contact 28 and second return contact 29 are both in contact with, or in communication with, first solid conductive cylindrical member 32. This configuration of ultrapolar telescopic electrosurgery handpiece/pencil 10 enables a user or surgeon to cut biological tissue with non-conductive sharp cutting tip 45, coagulate biological tissue with active contact 26 and return contact 28 on one side of electrosurgery blade 24, coagulate biological tissue with second active contact 27 and second return contact 29 on the other side of electrosurgery blade 24, and cut with active contact 26 and return contact 28 and with second active contact 27 and second return contact 29 on electrosurgery blade 24. The ultrapolar electrosurgery blade 24 is further described in detail in applicant's concurrently filed patent application entitled "Ultrapolar Electrosurgery Blade and Ultrapolar Electrosurgery Pencil" which is herein incorporated by reference in its entirety.

The ultrapolar telescopic electrosurgery handpiece/pencil 10 also includes a locking member 60 to lock the hollow telescopic member 18 in place relative to the handpiece member 12. In addition, as shown in FIGS. 1 and 2, ultrapolar telescopic electrosurgery handpiece/pencil 10 also includes at least one activation button 70 for cutting and at least one activation button 72 for coagulation.

FIG. 3 is a side perspective view of a second exemplary embodiment of the ultrapolar telescopic electrosurgery handpiece/pencil 100 of the present invention showing the interior components of the ultrapolar telescopic electrosurgery handpiece/pencil 100 as they would appear if one could see inside of the handpiece/pencil 100. Ultrapolar telescopic electrosurgery handpiece/pencil 100 includes a handpiece member 112 having a first end 114 and a second end 116, a hollow telescopic member 118 having a first end 120 and a second 122 where at least a portion of the hollow telescopic member 118 is concentrically positioned within the first end 114 of handpiece member 112, an electrosurgery blade 124 having both an active contact 126 and a return contact 128 positioned within the first end 120 of hollow telescopic member 118, a first solid conductive cylindrical member 130 in contact with active contact 126 of electrosurgery blade 124 and contained within the hollow telescopic member 118, a first hollow conductive tubular member 132 in contact with return contact 128 of electrosurgery blade 124 and contained within the hollow telescopic member 118, a second solid conductive cylindrical member 134 contained within the handpiece member 112 such that at least a portion of the second solid conductive cylindrical member 134 is contained within at least a portion of the first hollow conductive tubular member 132, and a second hollow conductive tubular member 136 contained within the handpiece member 112 such that at least a portion of the first solid conductive cylindrical member 130 is contained within at least a portion of the second hollow conductive tubular member 136. It will be understood by those skilled in the art that other means for connecting active contact 126 and return contact 128 of electrosurgery blade 124 to a circuit board located in or on handpiece member 112 for activating cutting and/or coagulation may be utilized, such as wires each coated with an insulator, for example, as long as the insulated wires are durable and capable of ensuring that the respective wires connected to the active and return contacts do not come into contact with one another. However, the solid conductive cylindrical members and the hollow conductive tubular members that are described with reference to the exemplary embodiments shown and described herein are considered to be a superior means for connecting the active and return contacts of the ultrapolar electrosurgery blade to the circuit board that enables activation of cutting and/or coagulation with the handpiece/pencil. In addition, the utilization of the solid conductive cylindrical members and the hollow conductive tubular members that are described with reference to the exemplary embodiments shown and described herein create a handpiece/pencil that is much less likely to be subject to failure and a handpiece/pencil that is much less likely to malfunction and result in an injury to a patient and or a user/surgeon during use of the handpiece/pencil.

As can be seen in the exemplary embodiment shown in FIG. 3, the electrosurgery pencil/handpiece 100 of the present invention has a handpiece member 112 and a hollow telescopic member 118 which both have channels therein that are in continuity with one another to enable evacuation of smoke and/or debris from the surgical site. During evacuation, the smoke and/or debris passes through the continuous channel and around the first and second solid conductive cylindrical members 130, 134 and the first and second hollow conductive tubular members 132, 136 that are contained in the continuous channel. In addition, a first support member 140 is positioned within the handpiece member 112 such that at least a portion of the second solid conductive cylindrical member 134 and at least a portion of the second hollow conductive tubular member 136 pass through the first support member 140. Further, a second support member 142 is positioned within the hollow telescopic member 118 such that at least a portion of the active contact 126 of electrosurgery blade 124 and at least a portion of return contact 128 of electrosurgery blade 124 pass through the second support member 142. The first and second hollow conductive tubular members 132, 136 and the first and second solid conductive cylindrical members 130, 134 may be made of stainless steel, copper, and/or titanium and the outer surfaces of the first and second hollow conductive tubular members 132, 136 may each be covered with an insulator.

The electrosurgery blade 124 is an ultrapolar electrosurgery blade having a non-conductive planar member with opposing planar sides and both an active contact 126 and a return contact 128 on each opposing planar side of the non-conductive planar member. The ultrapolar electrosurgery blade 124 further includes a non-conductive sharp cutting tip 145. The non-conductive sharp cutting tip 145 may be formed from the non-conductive planar member and both may made of a ceramic material.

Ultrapolar telescopic electrosurgery handpiece/pencil 100 also includes a swivel member 146 connected to the second end 116 of the handpiece member 112 such that the swivel member 146 rotates relative to the handpiece member 112. The swivel member 146 enables a vacuum tube 148 connected to the swivel member to twist about or around an electrical cord 150 connected to the handpiece member 112 thereby facilitating a surgeon's use of the ultrapolar telescopic electrosurgery handpiece/pencil 100 by reducing the drag or pulling down of the end of the ultrapolar telescopic electrosurgery handpiece/pencil 100 during electrosurgery.

FIG. 4 is the same as the view shown in FIG. 3 but with the ultrapolar telescopic electrosurgery handpiece/pencil 100 shown rotated 180 degrees relative to the swivel member 146 of the ultrapolar telescopic electrosurgery handpiece/pencil 100 which is maintained in the same position when the handpiece member 112 and the hollow telescopic member 118 of the ultrapolar telescopic electrosurgery handpiece/pencil 100 are rotated 180 degrees. As can be seen in FIG. 4, ultrapolar electrosurgery blade 124 also has a second active contact 127 and a second return contact 129 located on the opposing planar side of the non-conductive planar member that is opposite the opposing planar side that contains active contact 126 and return contact 128. As can be seen in FIGS. 3 and 4, active contact 126 and second active contact 127 are both in contact with, or in communication with, first solid conductive cylindrical member 130 and return contact 128 and second return contact 129 are both in contact with, or in communication with, first hollow conductive tubular member 132. This configuration of ultrapolar telescopic electrosurgery handpiece/pencil 100 enables a user or surgeon to cut biological tissue with non-conductive sharp cutting tip 145, coagulate biological tissue with active contact 126 and return contact 128 on one side of electrosurgery blade 124, coagulate biological tissue with second active contact 127 and second return contact 129 on the other side of electrosurgery blade 124, and cut with active contact 126 and return contact 128 and with second active contact 127 and second return contact 129 on electrosurgery blade 124. The ultrapolar electrosurgery blade 124 is further described in detail in applicant's concurrently filed patent application entitled "Ultrapolar Electrosurgery Blade and Ultrapolar Electrosurgery Pencil" which is herein incorporated by reference in its entirety.

The ultrapolar telescopic electrosurgery handpiece/pencil 100 also includes a locking member 160 to lock the hollow telescopic member 118 in place relative to the handpiece member 112. In addition, as shown in FIGS. 3 and 4, ultrapolar telescopic electrosurgery handpiece/pencil 100 also includes at least one activation button 170 for cutting and at least one activation button 172 for coagulation.

The detailed description of exemplary embodiments of the invention herein shows various exemplary embodiments of the invention. These exemplary embodiments and modes are described in sufficient detail to enable those skilled in the art to practice the invention and are not intended to limit the scope, applicability, or configuration of the invention in any way. Rather, the following disclosure is intended to teach both the implementation of the exemplary embodiments and modes and any equivalent modes or embodiments that are known or obvious to those reasonably skilled in the art. Additionally, all included examples are non-limiting illustrations of the exemplary embodiments and modes, which similarly avail themselves to any equivalent modes or embodiments that are known or obvious to those reasonably skilled in the art.

Other combinations and/or modifications of structures, arrangements, applications, proportions, elements, materials, or components used in the practice of the instant invention, in addition to those not specifically recited, can be varied or otherwise particularly adapted to specific environments, manufacturing specifications, design parameters, or other operating requirements without departing from the scope of the instant invention and are intended to be included in this disclosure.

Unless specifically noted, it is the Applicant's intent that the words and phrases in the specification and the claims be given the commonly accepted generic meaning or an ordinary and accustomed meaning used by those of ordinary skill in the applicable arts. In the instance where these meanings differ, the words and phrases in the specification and the claims should be given the broadest possible, generic meaning. If any other special meaning is intended for any word or phrase, the specification will clearly state and define the special meaning.

The invention claimed is:

1. An ultrapolar telescopic electrosurgery pencil comprising:
   a handpiece member having a first end and a second end;
   a hollow telescopic member having a first end and a second end wherein at least a portion of the hollow telescopic member is concentrically positioned within the first end of the handpiece member;
   an electrosurgery blade having both an active contact and a return contact positioned within the first end of the hollow telescopic member such that a passageway exists around the electrosurgery blade that is in communication with an area outside the first end of the hollow telescopic member;
   a first hollow conductive tubular member in contact with the active contact f the electrosurgery blade and contained within the hollow telescopic member;
   a first solid conductive cylindrical member in contact with the return contact of the electrosurgery blade and contained within the hollow telescopic member;
   a second hollow conductive tubular member contained within the handpiece member such that at least a portion of the first solid cylindrical member is contained within at least a portion of the second hollow conductive tubular member; and
   a second solid conductive cylindrical member contained within the handpiece member such that at least a portion of the second solid conductive cylindrical member is contained within at least a portion of the first hollow conductive tubular member.

2. The ultrapolar telescopic electrosurgery pencil of claim 1 wherein the handpiece member further comprises a smoke evacuation channel in communication with an interior of the hollow telescopic member for evacuating at least one of smoke and debris from the surgical site.

3. The ultrapolar telescopic electrosurgery pencil of claim 2 further comprising a first support member positioned within the handpiece member and having at least a portion of the second solid conductive cylindrical member and at least a portion of the second hollow conductive tubular member passing therethrough.

4. The ultrapolar telescopic electrosurgery pencil of claim 3 further comprising a second support member positioned within the hollow telescopic member and having at least a portion of the active contact of the electrosurgery blade and at least a portion of the return contact of the electrosurgery blade passing therethrough.

5. The ultrapolar telescopic electrosurgery pencil of claim 3 further comprising a swivel member connected to the second end of the handpiece member.

6. The ultrapolar telescopic electrosurgery pencil of claim 3 wherein the first and second hollow conductive tubular members each comprise an insulator on their outer surfaces.

7. The ultrapolar telescopic electrosurgery pencil of claim 3 wherein the electrosurgery blade comprises a non-conductive planar member having opposing planar sides with both an active contact and a return contact on each opposing planar side of the non-conductive planar member.

8. The ultrapolar telescopic electrosurgery pencil of claim 3 wherein the first and second hollow conductive tubular members and the first and second solid conductive cylindrical members comprise at least one of stainless steel, copper, and titanium.

9. The ultrapolar telescopic electrosurgery pencil of claim 3 further comprising a locking member to lock the hollow telescopic member in place relative to the handpiece member.

10. The ultrapolar telescopic electrosurgery handpiece of claim 3 wherein the handpiece comprises at least one activation button for cutting and at least one activation button for coagulation.

11. The ultrapolar telescopic electrosurgery pencil of claim 3 wherein the electrosurgery blade further comprises a non-conductive sharp cutting tip.

12. The ultrapolar telescopic electrosurgery pencil of claim 11 wherein the non-conductive sharp cutting tip comprises a ceramic material.

13. The ultrapolar telescopic electrosurgery pencil of claim 1 wherein either a portion of the return electrode is positioned within a hook shaped portion of the active electrode or a portion of the active electrode is positioned within a hook shaped portion of the return electrode.

14. An ultrapolar telescopic electrosurgery pencil comprising:
   a handpiece having a first end and second end;
   a hollow telescopic tubular member having a first end and a second end wherein at least a portion of the hollow telescopic member is concentrically positioned within the first end of the handpiece member;
   an electrosurgery blade having both an active contact and a return contact positioned within the first end of the hollow telescopic tubular member, such that a passageway exists around the electrosurgery blade that is in communication with an area outside the first end of the hollow telescopic member;
   a first solid conductive cylindrical member in contact with the active contact of the electrosurgery blade and contained within the hollow telescopic tubular member;
   a first hollow conductive tubular member in contact with the return contact of the electrosurgery blade and contained within the hollow telescopic tubular member;
   a second solid conductive cylindrical member contained within the handpiece member such that at least a portion of the second solid cylindrical member is contained within at least a portion of the first hollow conductive tubular member; and
   a second hollow conductive tubular member contained within the handpiece member such that at least a portion of the first solid cylindrical member is contained within at least a portion of the second hollow conductive tubular member.

15. The ultrapolar telescopic electrosurgery pencil of the claim 14 wherein the handpiece member further comprises a smoke evacuation channel in communication with an interior of the hollow telescopic tubular member for evacuating at least one of smoke and debris form the surgical site.

16. The ultrapolar electrosurgery pencil of claim 15 further comprising a first support member positioned within the handpiece member and having at least a portion of the second solid cylindrical member and at least a portion of the second hollow conductive tubular member passing therethrough.

17. The ultrapolar telescopic electrosurgery pencil of claim 16 further comprising a second support member positioned within the hollow telescopic member and having at least a portion of the active contact of the electrosurgery blade and at least a portion of the return contact of the electrosurgery blade passing therethrough.

18. The ultrapolar telescopic electrosurgery pencil of claim 16 fitrther comprising a swivel member connected to the second end of the handpiece member.

19. The ultrapolar telescopic electrosurgery pencil of claim 16 wherein the first and second hollow conductive tubular members each comprise an insulator on their outer surfaces.

20. The ultrapolar telescopic electrosurgery pencil of claim 16 wherein the electrosurgery blade comprises a non-conductive planar member having opposing planar sides with both an active contact and a return contact on each opposing planar side of the non-conductive planar member.

21. The ultrapolar telescopic electrosurgery pencil of claim 16 further comprising a locking member to lock the hollow telescopic tubular member in place relative to the handpiece member.

22. The ultrapolar telescopic electrosurgery handpiece of claim 16 wherein the handpiece comprises at least one activation button for cutting and at least one activation button for coagulation.

23. The ultrapolar telescopic electrosurgery pencil of claim 16 wherein the electrosurgery blade further comprises a non-conductive sharp cutting tip.

24. The ultrapolar telescopic electrosurgery pencil of claim 23 wherein the non-conductive sharp cutting tip comprises a ceramic material.

25. The ultrapolar telescopic electrosurgery pencil of claim 14 wherein either a portion of the return electrode is positioned within a hook shaped portion of the active electrode or a portion of the active electrode is positioned within a hook shaped portion of the return electrode.

* * * * *